(12) United States Patent
Sakuda et al.

(10) Patent No.: US 9,773,638 B2
(45) Date of Patent: Sep. 26, 2017

(54) SPECIMEN PREPARATION DEVICE

(71) Applicant: JEOL Ltd., Tokyo (JP)

(72) Inventors: Yusuke Sakuda, Tokyo (JP); Shunsuke Asahina, Tokyo (JP)

(73) Assignee: JEOL Ltd., Tokyo (JP)

( * ) Notice: Subject to any disclaimer, the term of this patent is extended or adjusted under 35 U.S.C. 154(b) by 15 days.

(21) Appl. No.: 14/945,630

(22) Filed: Nov. 19, 2015

(65) Prior Publication Data
US 2016/0148779 A1 May 26, 2016

(30) Foreign Application Priority Data
Nov. 21, 2014 (JP) ................. 2014-236569

(51) Int. Cl.
H01J 37/147 (2006.01)
G01N 1/32 (2006.01)
H01J 37/305 (2006.01)
H01J 37/08 (2006.01)
H01J 37/20 (2006.01)

(52) U.S. Cl.
CPC ............ *H01J 37/1478* (2013.01); *G01N 1/32* (2013.01); *H01J 37/08* (2013.01); *H01J 37/20* (2013.01); *H01J 37/3053* (2013.01); *H01J 2237/022* (2013.01); *H01J 2237/0213* (2013.01); *H01J 2237/3146* (2013.01); *H01J 2237/3151* (2013.01)

(58) Field of Classification Search
CPC .. H01J 37/02; H01J 37/08; H01J 37/09; H01J 37/28; H01J 37/20; H01J 37/305; H01J 37/317; H01J 37/3171; H01J 37/3053; H01J 37/1478; H01J 2237/022; H01J 2237/063; H01J 2237/0213; H01J 2237/0203; H01J 2237/0245; H01J 2237/3146; H01J 2237/3151; H01J 2237/0805; H01J 2237/31749; H01J 2237/31745
See application file for complete search history.

(56) References Cited

U.S. PATENT DOCUMENTS

| 5,466,941 A * | 11/1995 | Kim ................. H01J 27/028 204/298.04 |
| 5,986,264 A | 11/1999 | Grunewald |
| 2005/0045834 A1 | 3/2005 | McGinn et al. |
| 2005/0118065 A1* | 6/2005 | Hasegawa .............. H01J 37/28 422/502 |
| 2005/0232726 A1 | 10/2005 | Murrell |

FOREIGN PATENT DOCUMENTS

JP 4922632 B2 4/2012

OTHER PUBLICATIONS

Extended European Search Report re EP 15195033.4 dated Apr. 13, 2016.

* cited by examiner

Primary Examiner — David E Smith
Assistant Examiner — Hsien Tsai
(74) Attorney, Agent, or Firm — The Webb Law Firm

(57) ABSTRACT

A specimen preparation device prepares a cross section of a specimen by applying an ion beam, the specimen preparation device including: an ion beam generator that generates the ion beam; a specimen holder that holds the specimen; a shield plate that shields part of the specimen from the ion beam; and a tilted plate that is placed to intersect a path of the ion beam on a downstream side of the specimen, and has an incidence surface that is tilted relative to a direction in which the ion beam is incident.

9 Claims, 13 Drawing Sheets

SPECIMEN PREPARATION DEVICE

Japanese Patent Application No. 2014-236569, filed on Nov. 21, 2014, is hereby incorporated by reference in its entirety.

BACKGROUND OF THE INVENTION

The present invention relates to a specimen preparation device.

A specimen preparation device (ion beam processing device) that utilizes an ion beam is known as a device that prepares a cross section of a specimen that is observed or analyzed using an electron microscope, an electron probe microanalyser (EPMA), an Auger microprobe, or the like.

For example, Japanese Patent No. 4922632 discloses a specimen preparation device that prepares a cross section of a specimen by covering part of the specimen with a shield material, and milling part of the specimen that is not covered with the shield material by applying an ion beam to the specimen (including the edge of the shield material) (from the side where the shield material is provided).

Such a specimen preparation device is designed so that the ion beam is applied to the specimen in a vacuum chamber. In this case, the ion beam that has passed by the specimen without being applied to the specimen may be applied to the inner bottom surface of the vacuum chamber, and the inner bottom surface of the vacuum chamber may be sputtered to contaminate the specimen. The above problem is described below with reference to the drawings.

FIGS. 13 and 14 are views schematically illustrating a state inside a vacuum chamber of a specimen preparation device.

As illustrated in FIG. 13, an ion beam generated by an ion beam generator 4 is applied to a specimen 2 that is partially covered with a shield plate 6. The area of the specimen 2 that is not covered with the shield plate 6 is thus mill to prepare a cross section of the specimen 2.

As illustrated in FIG. 14, when the ion beam is applied to an inner bottom surface 8 of the vacuum chamber after the specimen 2 has been mill, the inner bottom surface 8 of the vacuum chamber is sputtered, and the material that forms the inner bottom surface 8 of the vacuum chamber adheres to a surface 2*a* (i.e., the surface of the specimen 2 opposite to the surface on which the shield plate 6 is placed) of the specimen 2. As a result, the surface 2*a* of the specimen 2 is contaminated.

Specifically, a known specimen preparation device has a problem in that the surface 2*a* of the specimen 2 may be contaminated, and it may be impossible to observe both the cross section and the surface of a single specimen, for example.

SUMMARY

Several aspects of the invention may provide a specimen preparation device that can reduce contamination of a specimen.

According to a first aspect of the invention, there is provided a specimen preparation device that prepares a cross section of a specimen by applying an ion beam, the specimen preparation device including:

an ion beam generator that generates the ion beam;
a specimen holder that holds the specimen;
a shield plate that shields part of the specimen from the ion beam; and a tilted plate that is placed to intersect a path of the ion beam on a downstream side of the specimen, and has an incidence surface that is tilted relative to a direction in which the ion beam is incident.

According to a second aspect of the invention, there is provided a specimen preparation device that prepares a cross section of a specimen by applying an ion beam, the specimen preparation device including:

an ion beam generator that generates the ion beam;
a specimen holder that holds the specimen;
a shield plate that shields part of the specimen from the ion beam;
a tilted plate that is placed to intersect a path of the ion beam on a downstream side of the specimen, and has an incidence surface on which the ion beam is incident; and
a tilted plate support that supports the tilted plate so that a tilt angle of the incidence surface relative to the ion beam can be changed.

Figure 1:
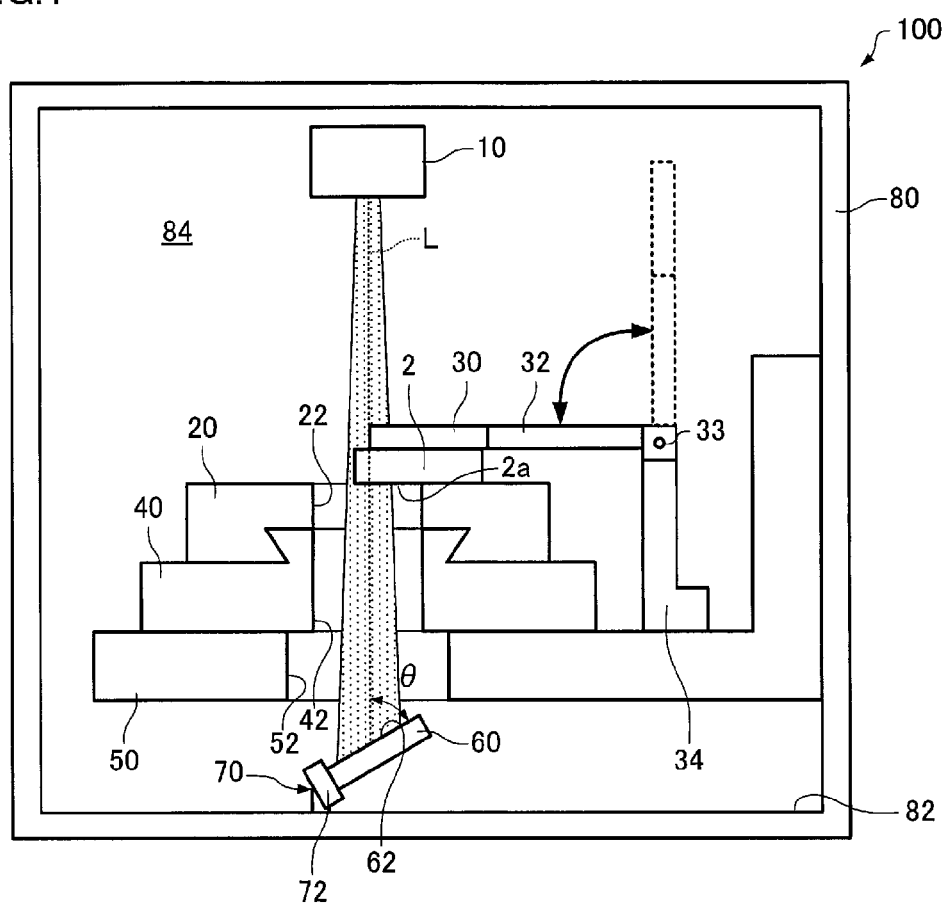
FIG. 1 schematically illustrates the configuration of a specimen preparation device according to the first embodiment.

DETAILED DESCRIPTION OF THE EMBODIMENT (1) According to one embodiment of the invention, a specimen preparation device prepares a cross section of a specimen by applying an ion beam, the specimen preparation device including:

an ion beam generator that generates the ion beam;
a specimen holder that holds the specimen;

a shield plate that shields part of the specimen from the ion beam; and a tilted plate that is placed to intersect a path of the ion beam on a downstream side of the specimen, and has an incidence surface that is tilted relative to a direction in which the ion beam is incident.

Since the specimen preparation device includes the tilted plate that is placed to intersect the path of the ion beam on the downstream side of the specimen, it is possible to prevent a situation in which the ion beam is applied to the inner bottom surface of the vacuum chamber, or reduce the area of the inner bottom surface of the vacuum chamber to which the ion beam is applied, for example. Therefore, the specimen preparation device can reduce a situation in which the material that forms the inner bottom surface of the vacuum chamber is sputtered by the ion beam, and adheres to the surface of the specimen to contaminate the specimen.

(2) In the specimen preparation device, the incidence surface and the specimen may not overlap each other when viewed in the direction perpendicular to the incidence surface.

When the incidence surface of the tilted plate and the specimen do not overlap each other when viewed in the direction perpendicular to the incidence surface of the tilted plate, it is possible to prevent a situation in which the material that forms the tilted plate that has been sputtered by the ion beam adheres to the surface of the specimen, or reduce the amount of the material that forms the tilted plate that adheres to the surface of the specimen.

(3) In the specimen preparation device, the incidence surface may be formed of diamond.

When the incidence surface is formed of diamond, the tilted plate is not easily sputtered by the ion beam.

(4) In the specimen preparation device, the incidence surface and the specimen may overlap each other when viewed in the direction perpendicular to the incidence surface.

When the incidence surface of the tilted plate and the specimen overlap each other when viewed in the direction perpendicular to the incidence surface of the tilted plate, the material that forms the tilted plate that has been sputtered by the ion beam applied to the incidence surface can be caused to adhere to the surface of the specimen. The specimen preparation device can thus form the desired film on the surface of the specimen while preparing a cross section of the specimen.

(5) In the specimen preparation device, the incidence surface may be formed of graphite.

When the incidence surface is formed of graphite, a carbon film can be formed on the surface of the specimen. Therefore, the specimen preparation device can prepare a cross section of the specimen that is observed or analyzed using an electron microscope while forming a carbon film that exhibits an antistatic effect when observing or analyzing the specimen using an electron microscope or the like, for example.

(6) The specimen preparation device may further include a vacuum chamber in which the specimen is placed, and the tilted plate may be placed between the specimen and the inner bottom surface of the vacuum chamber.

When the tilted plate is placed between the specimen and the inner bottom surface of the vacuum chamber, it is possible to prevent a situation in which the ion beam is applied to the inner bottom surface of the vacuum chamber, or reduce the area of the inner bottom surface of the vacuum chamber to which the ion beam is applied, for example. Therefore, the specimen preparation device can reduce a situation in which the material that forms the inner bottom surface of the vacuum chamber is sputtered by the ion beam, and adheres to the surface of the specimen to contaminate the specimen.

(7) The specimen preparation device may further include a tilted plate support that supports the tilted plate so that the tilt angle of the incidence surface relative to the ion beam can be changed.

In this case, the specimen preparation device can change the tilt angle of the incidence surface.

(8) According to another embodiment of the invention, a specimen preparation device prepares a cross section of a specimen by applying an ion beam, the specimen preparation device including:

an ion beam generator that generates the ion beam;

a specimen holder that holds the specimen;

a shield plate that shields part of the specimen from the ion beam;

a tilted plate that is placed to intersect a path of the ion beam on a downstream side of the specimen, and has an incidence surface on which the ion beam is incident; and a tilted plate support that supports the tilted plate so that the tilt angle of the incidence surface relative to the ion beam can be changed.

Since the specimen preparation device includes the tilted plate that is placed to intersect the path of the ion beam on the downstream side of the specimen, it is possible to prevent a situation in which the ion beam is applied to the inner bottom surface of the vacuum chamber, or reduce the area of the inner bottom surface of the vacuum chamber to which the ion beam is applied, for example. Therefore, the specimen preparation device can reduce a situation in which the material that forms the inner bottom surface of the vacuum chamber is sputtered by the ion beam, and adheres to the surface of the specimen to contaminate the specimen.

Since the specimen preparation device is configured so that the tilted plate can be supported by the tilted plate support so that the incidence surface of the tilted plate and the specimen do not overlap each other when viewed in the direction perpendicular to the incidence surface of the tilted plate, it is possible to prevent a situation in which the material that forms the tilted plate that has been sputtered by the ion beam adheres to the surface of the specimen, or reduce the amount of the material that forms the tilted plate that adheres to the surface of the specimen, for example.

Since the specimen preparation device is configured so that the tilted plate can be supported by the tilted plate support so that the incidence surface of the tilted plate and the specimen overlap each other when viewed in the direction perpendicular to the incidence surface of the tilted plate, the material that forms the tilted plate that has been sputtered by the ion beam applied to the incidence surface can be caused to adhere to the surface of the specimen, for example. The specimen preparation device can thus form the desired film on the surface of the specimen while preparing a cross section of the specimen.

(9) In the specimen preparation device, the incidence surface may be formed of diamond-like carbon.

When the incidence surface is formed of diamond-like carbon, the tilted plate is not easily sputtered by the ion beam when the tilted plate support supports the tilted plate so that the incidence surface and the specimen do not overlap each other when viewed in the direction perpendicular to the incidence surface.

When the incidence surface is formed of diamond-like carbon, a conductive film can be formed on the surface of the specimen when the tilted plate support supports the tilted plate so that the incidence surface and the specimen overlap each other when viewed in the direction perpendicular to the incidence surface. Therefore, the specimen preparation device can prepare a cross section of the specimen that is observed or analyzed using an electron microscope while forming a conductive film that exhibits an antistatic effect when observing or analyzing the specimen using an electron microscope or the like, for example.

Exemplary embodiments of the invention are described in detail below with reference to the drawings. Note that the following exemplary embodiments do not unduly limit the scope of the invention as stated in the claims. Note also that all of the elements described below should not necessarily be taken as essential elements of the invention.

1. First Embodiment

A specimen preparation device according to a first embodiment of the invention is described below with reference to the drawings. FIG. 1 schematically illustrates the configuration of a specimen preparation device 100 according to the first embodiment.

The specimen preparation device 100 is a device that applies an ion beam to a specimen 2 to prepare a cross section of the specimen 2. The specimen preparation device 100 can prepare a cross section of a specimen that is observed or analyzed using a scanning electron microscope (SEM), a transmission electron microscope (TEM), a scanning transmission electron microscope (STEM), an electron probe microanalyser (EPMA), an Auger microprobe, or the like, for example.

As illustrated in FIG. 1, the specimen preparation device 100 includes an ion beam generator 10, a specimen holder 20, a shield plate 30, a shield plate holding section 32, a shield plate position adjustment section 34, a specimen position adjustment section 40, a specimen stage 50, a tilted plate 60, a tilted plate support 70, and a vacuum chamber 80.

The ion beam generator 10 generates an ion beam. The ion beam generator 10 is provided to the upper part of the vacuum chamber 80. The ion beam generator 10 is an ion gun, for example. The ion beam generator 10 emits the ion beam while accelerating the ion beam at a predetermined accelerating voltage (e.g., about 2 to 6 kV). An Ar ion beam may be used as the ion beam, for example. The diameter of the ion beam is about several hundreds of micrometers, for example.

The specimen holder 20 holds the specimen 2. The specimen holder 20 is attached to the specimen position adjustment section 40. A through-hole 22 is formed in the specimen holder 20. Part of the specimen 2 is placed over the through-hole 22 (so as to overlap the through-hole 22).

The shield plate 30 is a member that shields part of the specimen 2 from the ion beam. The shield plate 30 shields the non-processing target area of the specimen 2 from the ion beam. Therefore, the area of the specimen 2 that is not covered with the shield plate 30 is mill to prepare a cross section of the specimen 2.

The shield plate holding section 32 is a member that holds the shield plate 30. The shield plate holding section 32 can rotate around a rotation shaft 33. Therefore, the shield plate holding section 32 can move the shield plate 30 from the vertical position to the horizontal position, or move the shield plate 30 from the horizontal position to the vertical position. The shield plate 30 can thus be set to the horizontal position so as to be placed on the specimen 2, or set to the vertical position so as to move away from the specimen 2.

The shield plate position adjustment section 34 can move the shield plate 30. The milling target area of the specimen 2 can be determined by moving the shield plate 30 in the horizontal direction using the shield plate position adjustment section 34.

The specimen position adjustment section 40 can move the specimen holder 20 in the horizontal direction. The specimen 2 can be positioned by moving the specimen holder 20 using the specimen position adjustment section 40 to move the specimen 2 held by the specimen holder 20.

The specimen stage 50 is attached to the side wall of the vacuum chamber 80. The shield plate holding section 32 and the specimen position adjustment section 40 are attached to the specimen stage 50.

The through-hole 22, a through-hole 42, and a through-hole 52 are respectively formed in the specimen holder 20, the specimen position adjustment section 40, and the specimen stage 50. The through-hole 22 formed in the specimen holder 20 communicates with the through-hole 52 formed in the specimen stage 50 through the through-hole 42 formed in the specimen position adjustment section 40. The through-hole 22, the through-hole 42, and the through-hole 52 form one through-hole that allows the ion beam to pass through.

The specimen 2 is placed on the specimen holder 20 so that the end of the specimen 2 that is processed using the ion beam is situated over the through-hole 22. The ion beam that has been generated by the ion beam generator 10 and has passed by the specimen 2 without being applied to the specimen 2 (without being blocked by the specimen 2) is applied to the tilted plate 60 through the through-hole 22, the through-hole 42, and the through-hole 52.

The tilted plate 60 is placed to intersect the path of the ion beam on the downstream side of the specimen 2. Note that the expression "on the downstream side of the specimen 2" used herein in connection with the tilted plate 60 means that the tilted plate 60 is situated to intersect the path of the ion beam on the downstream side relative to the specimen 2. The expression "on the downstream side of the specimen 2" used herein in connection with the tilted plate 60 means that the tilted plate 60 is situated away from the ion beam generator 10 as compared with the specimen 2. The tilted plate 60 is situated on the path of the ion beam that has been generated by the ion beam generator 10 and has passed by the specimen 2 without being applied to the specimen 2. Note that the path of the ion beam on which the tilted plate 60 is situated also includes a position through which the ion beam passes as a result of milling the specimen 2 using the ion beam.

In the example illustrated in FIG. 1, the tilted plate 60 is placed between the specimen 2 and an inner bottom surface 82 of the vacuum chamber 80. The tilted plate 60 is placed under the through-hole 52. Specifically, the tilted plate 60 and the through-hole 52 overlap each other when viewed in the travel direction of the ion beam. The tilted plate 60 is desirably placed between the specimen 2 and the inner bottom surface 82 of the vacuum chamber 80 at a position close to the inner bottom surface 82 of the vacuum chamber 80 (i.e., at a position away from the specimen 2), for example. In this case, the material that forms the tilted plate 60 rarely adheres to a surface 2a of the specimen 2 when the tilted plate 60 is sputtered by the ion beam as compared with the case where the tilted plate 60 is placed close to the specimen 2, for example.

The tilted plate 60 is a plate-like member. The shape of the tilted plate 60 is not particularly limited. The tilted plate 60 may be in the shape of a rectangular parallelepiped, a column, a polygonal prism, or the like. The tilted plate 60 has an incidence surface 62 to which the ion beam that has passed by the specimen 2 without being applied to the specimen 2 is applied (i.e., on which the ion beam that has passed by the specimen 2 without being applied to the specimen 2 is incident). The incidence surface 62 is the surface of the tilted plate 60 to which the ion beam is applied. The incidence surface 62 is a flat and smooth surface.

The incidence surface 62 is tilted relative to the direction in which the ion beam is incident. Specifically, the angle (tilt angle) θ formed by the incidence surface 62 and an optical axis L of the ion beam (i.e., the center axis of the ion beam) is other than 0° and 90° (θ≠0°, 90°). The tilted plate 60 is placed so that the incidence surface 62 does not face the specimen 2. Specifically, the incidence surface 62 and the specimen 2 do not overlap each other when viewed in the direction perpendicular (normal) to the incidence surface 62.

The incidence surface 62 is formed of diamond, for example. The entire tilted plate 60 may be formed of diamond, or part of the tilted plate 60 that forms the incidence surface 62 may be formed of diamond. The incidence surface 62 may be formed of a material other than diamond. The incidence surface 62 is desirably formed of a material (e.g., hard single-crystal material or amorphous material) that is not easily sputtered (etched) by the ion beam.

The tilted plate support 70 supports the tilted plate 60. In the example illustrated in FIG. 1, the tilted plate support 70 is attached to the inner bottom surface 82 of the vacuum chamber 80. Note that the tilted plate support 70 may be attached to the specimen stage 50, the specimen position adjustment section 40, the specimen holder 20, or the like as long as the tilted plate support 70 can support the tilted plate 60.

The tilted plate support 70 includes a tilted plate holder 72 to which the tilted plate 60 is attached. The tilted plate 60 is attached to the tilted plate holder 72 so that the tilted plate 60 can be replaced. Specifically, the specimen preparation device 100 is designed so that the tilted plate 60 can be easily replaced.

The vacuum chamber 80 is evacuated using an evacuation device (not illustrated in FIG. 1). A processing chamber 84 inside the vacuum chamber 80 can thus be set to a vacuum state (decompressed state). The specimen 2 is placed inside the processing chamber 84. The specimen 2 is processed inside the processing chamber 84 by applying the ion beam to the specimen 2.

Figure 2:
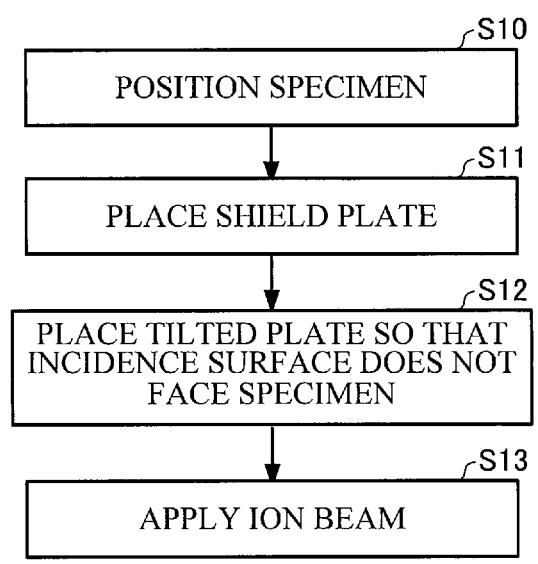
FIG. 2 is a flowchart illustrating an example of a specimen preparation method that utilizes a specimen preparation device according to the first embodiment.
Figure 3:
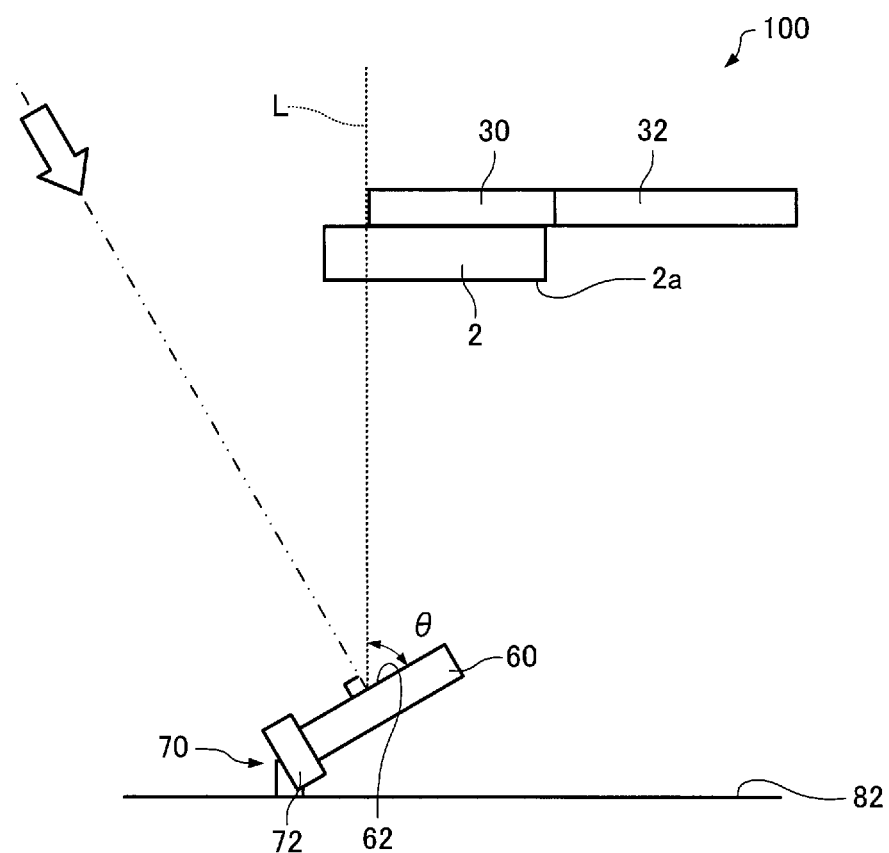
FIG. 3 illustrates the operation of a specimen preparation device according to the first embodiment.
Figure 4:
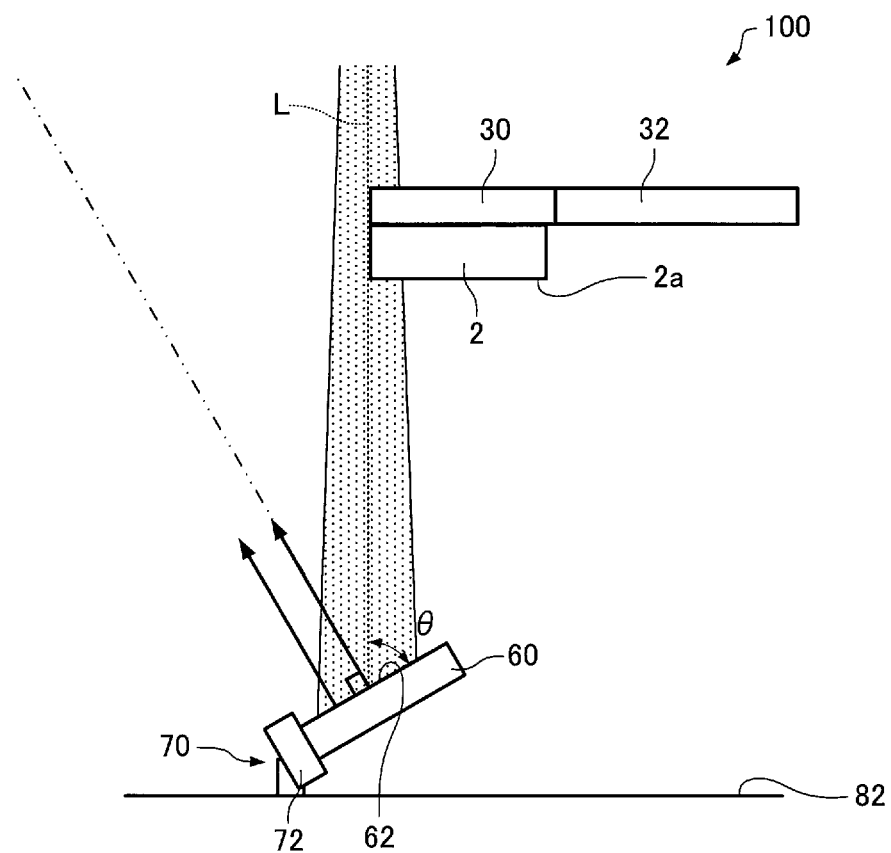
FIG. 4 illustrates the operation of a specimen preparation device according to the first embodiment.

The operation of the specimen preparation device 100 is described below. FIG. 2 is a flowchart illustrating an example of a specimen preparation method that utilizes the specimen preparation device 100. FIGS. 3 and 4 illustrate the operation of the specimen preparation device 100. Note that the members of the specimen preparation device 100 other than the shield plate 30, the shield plate holding section 32, the tilted plate 60, and the tilted plate support 70 are omitted in FIGS. 3 and 4.

In a step S10, the specimen 2 is positioned.

Specifically, the specimen 2 is mounted on the specimen holder 20. The specimen 2 is mounted on the specimen holder 20 so as to be situated over the through-hole 22. The specimen 2 is moved using the specimen position adjustment section 40 to position the specimen 2 so that the ion beam is applied to the milling target area of the specimen 2.

The shield plate 30 is then placed on the specimen 2 (step S11).

Specifically, the shield plate 30 is placed on the specimen 2 by moving the shield plate 30 held by the shield plate holding section 32 from the vertical position to the horizontal position. The shield plate 30 is moved using the shield plate position adjustment section 34 to position the shield plate 30.

The tilted plate 60 is then placed so that the incidence surface 62 of the tilted plate 60 does not face the specimen 2 (step S12).

Specifically, the tilted plate 60 is placed so that the incidence surface 62 and the specimen 2 do not overlap each other when viewed in the direction perpendicular to the incidence surface 62 (see the arrow illustrated in FIG. 3). The tilted plate 60 can thus be placed so that the incidence surface 62 of the tilted plate 60 does not face the specimen 2. The tilted plate 60 is placed to intersect the path of the ion beam on the downstream side of the specimen 2. The tilted plate 60 is placed so that the incidence surface 62 is tilted relative to the direction in which the ion beam is incident. The tilted plate 60 can be placed at a predetermined position by attaching the tilted plate 60 to the tilted plate holder 72.

Note that the step that places the tilted plate 60 (step S12) may be performed before the step that positions the specimen 2 (step S10) as long as the step that places the tilted plate 60 (step S12) is performed before the step that applies the ion beam (step S13).

The ion beam is then applied to the specimen 2 (step S13).

The ion beam is generated by the ion beam generator 10, and applied to the specimen 2.

As illustrated in FIG. 4, the part of the specimen 2 that is not covered with the shield plate 30 is gradually mill by the ion beam. For example, the ion beam is applied until the part of the specimen 2 that is not covered with the shield plate 30 is completely removed.

The amount of the ion beam that passes by the specimen 2 increases as the specimen 2 is mill by the applied ion beam. The ion beam that has passed by the specimen 2 is applied to the tilted plate 60 through the through-hole 22, the through-hole 42, and the through-hole 52.

The material that forms the tilted plate 60 is sputtered when the ion beam is applied to the incidence surface 62 of the tilted plate 60. In this case, most of the material that forms the tilted plate 60 that has been sputtered travels in the direction perpendicular to the incidence surface 62 (see FIG. 4). Since the tilted plate 60 is placed so that the incidence surface 62 and the specimen 2 do not overlap each other when viewed in the direction perpendicular to the incidence surface 62, it is possible to suppress a situation in which the material that forms the tilted plate 60 that has been sputtered adheres to the surface 2a of the specimen 2. Note that the tilted plate 60 can prevent the ion beam from being applied to the inner bottom surface 82 of the vacuum chamber 80, or reduce the area of the inner bottom surface 82 of the vacuum chamber 80 to which the ion beam is applied as compared with the case where the tilted plate 60 is not placed.

A cross section of the specimen 2 can be prepared using the specimen preparation device 100 by performing the above steps.

The specimen preparation device 100 has the following features, for example.

The specimen preparation device 100 includes the tilted plate 60 that is placed to intersect the path of the ion beam on the downstream side of the specimen 2, and has the incidence surface 62 that is tilted relative to the direction in which the ion beam is incident.

For example, when the tilted plate 60 is not provided, the ion beam that has passed by the specimen 2 is applied to the inner bottom surface 82 of the vacuum chamber 80, and the inner bottom surface 82 of the vacuum chamber 80 is sputtered. In this case, the material that forms the inner bottom surface 82 of the vacuum chamber 80 adheres to the surface 2a of the specimen 2, and contaminates the surface 2a of the specimen 2.

Since the specimen preparation device 100 includes the tilted plate 60 that is placed to intersect the path of the ion beam on the downstream side of the specimen 2, the ion beam is not applied to the inner bottom surface 82 of the vacuum chamber 80, or the area of the inner bottom surface 82 of the vacuum chamber 80 to which the ion beam is applied can be reduced. Therefore, the specimen preparation device 100 can reduce a situation in which the material that forms the inner bottom surface 82 of the vacuum chamber 80 is sputtered by the ion beam, and adheres to the surface 2a of the specimen 2 to contaminate the specimen 2. Therefore, both the cross section and the surface 2a of the specimen prepared using the specimen preparation device 100 can be observed or analyzed, for example.

The specimen preparation device 100 is configured so that the incidence surface 62 of the tilted plate 60 and the specimen 2 do not overlap each other when viewed in the direction perpendicular to the incidence surface 62 of the tilted plate 60. This makes it possible to prevent a situation in which the material that forms the tilted plate 60 that has been sputtered by the ion beam adheres to the surface 2a of the specimen 2, or reduce the amount of the material that forms the tilted plate 60 that adheres to the surface 2a of the specimen 2.

The incidence surface 62 of the tilted plate 60 included in the specimen preparation device 100 is formed of diamond. Therefore, the tilted plate 60 is not easily sputtered by the ion beam.

The specimen preparation device 100 includes the vacuum chamber 80 in which the specimen 2 is placed, and the tilted plate 60 is placed between the specimen 2 and the inner bottom surface 82 of the vacuum chamber 80. Therefore, the specimen preparation device 100 can prevent a situation in which the ion beam is applied to the inner bottom surface 82 of the vacuum chamber 80, or reduce the area of the inner bottom surface 82 of the vacuum chamber 80 to which the ion beam is applied.

2. Second Embodiment

Figure 5:
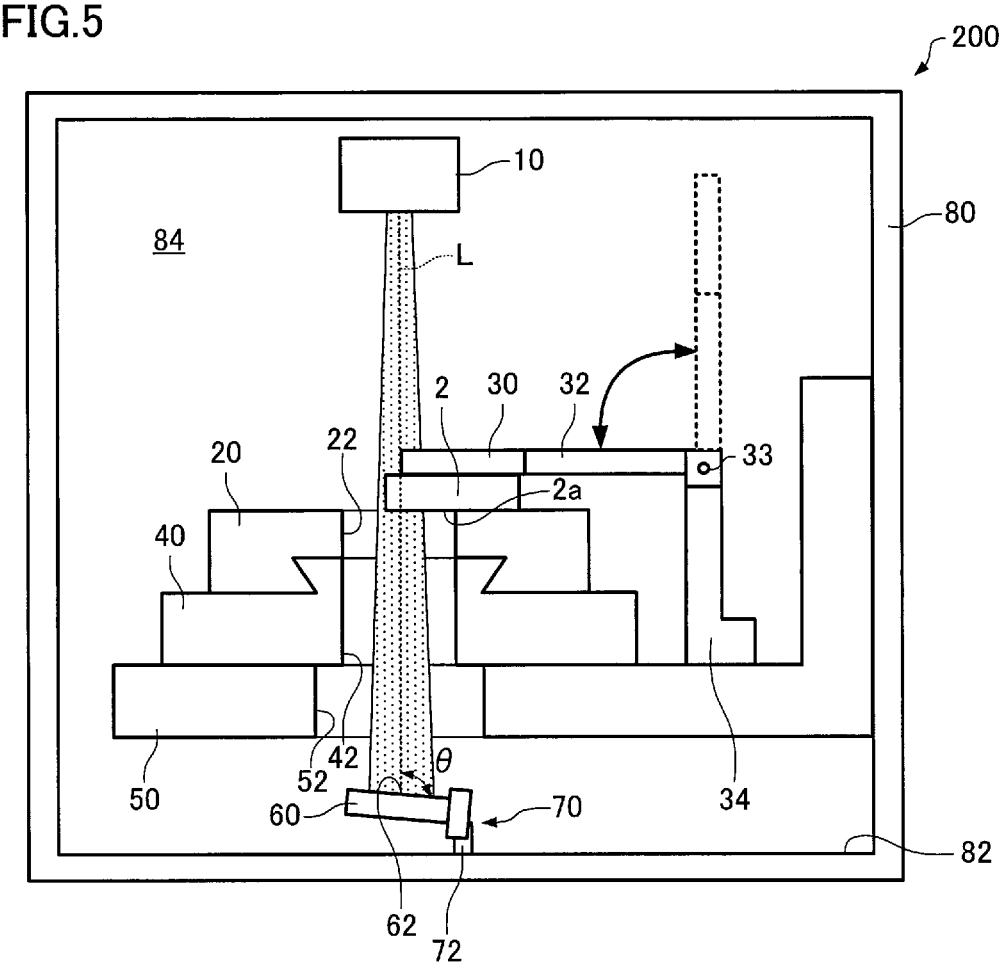
FIG. 5 schematically illustrates the configuration of a specimen preparation device according to the second embodiment.

A specimen preparation device according to a second embodiment of the invention is described below with reference to the drawings. FIG. 5 schematically illustrates the configuration of a specimen preparation device 200 according to the second embodiment. Note that the members of the specimen preparation device 200 according to the second embodiment that are identical in function to those of the specimen preparation device 100 according to the first embodiment are indicated by the same reference signs, and detailed description thereof is omitted.

The specimen preparation device 100 is configured so that the incidence surface 62 of the tilted plate 60 and the specimen 2 do not overlap each other when viewed in the direction perpendicular to the incidence surface 62 of the tilted plate 60 (see FIG. 1).

As illustrated in FIG. 5, the specimen preparation device 200 is configured so that the incidence surface 62 of the tilted plate 60 and the specimen 2 overlap each other when viewed in the direction perpendicular to the incidence surface 62 of the tilted plate 60. Specifically, the tilted plate 60 is placed so that the incidence surface 62 faces the specimen 2.

The incidence surface 62 of the tilted plate 60 is formed of graphite, for example. Therefore, when the ion beam is applied to the incidence surface 62, graphite is sputtered and adheres to (is deposited on) the surface 2a of the specimen 2. The incidence surface 62 may be formed of a material other than graphite. The material for forming the incidence surface 62 may be appropriately selected taking account of the material that is caused to adhere to the surface 2a of the specimen 2 (i.e., a film (material) that is deposited on the surface 2a).

Figure 6:
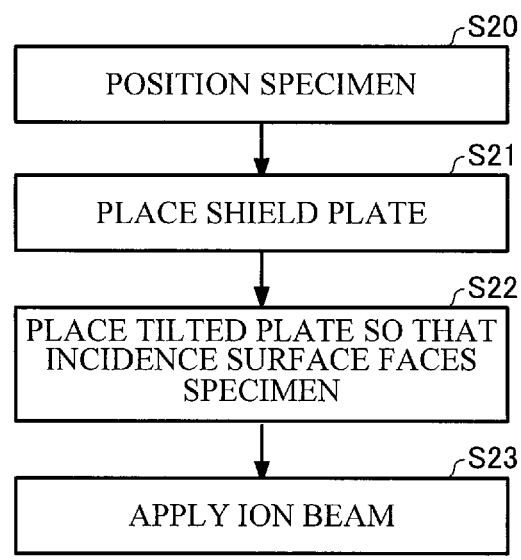
FIG. 6 is a flowchart illustrating an example of a specimen preparation method that utilizes a specimen preparation device according to the second embodiment.
Figure 7:
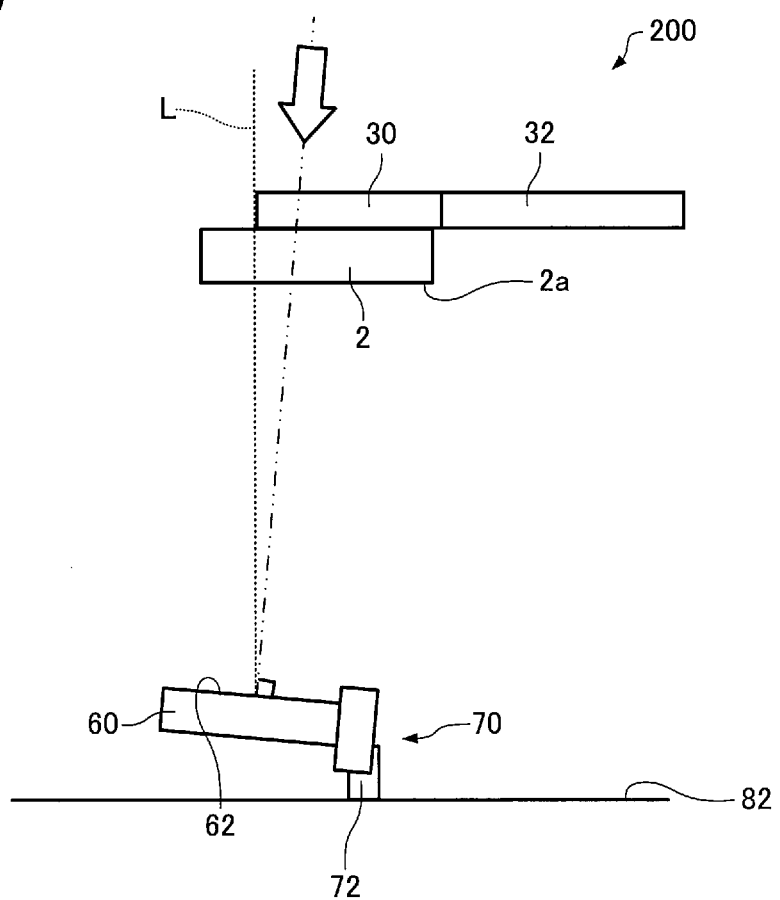
FIG. 7 illustrates the operation of a specimen preparation device according to the second embodiment.
Figure 8:
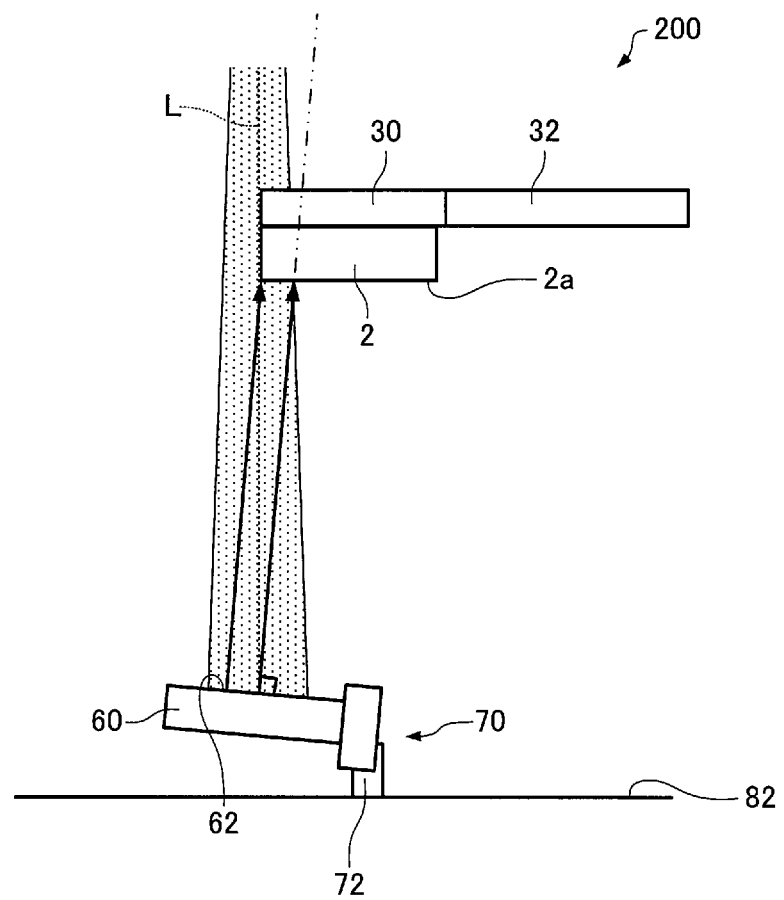
FIG. 8 illustrates the operation of a specimen preparation device according to the second embodiment.

The operation of the specimen preparation device 200 is described below. FIG. 6 is a flowchart illustrating an example of a specimen preparation method that utilizes the specimen preparation device 200. FIGS. 7 and 8 illustrate the operation of the specimen preparation device 200. Note that the members of the specimen preparation device 200 other than the shield plate 30, the shield plate holding section 32, the tilted plate 60, and the tilted plate support 70 are omitted in FIGS. 7 and 8.

In a step S20, the specimen 2 is positioned.

The step that positions the specimen 2 (step S20) is performed in the same manner as the step that positions the specimen 2 (step S10) illustrated in FIG. 2.

The shield plate 30 is then placed on the specimen 2 (step S21).

The step that places the shield plate 30 (step S21) is performed in the same manner as the step that places the shield plate 30 (step S11) illustrated in FIG. 2.

The tilted plate 60 is then placed so that the incidence surface 62 of the tilted plate 60 faces the specimen 2 (step S22).

Specifically, the tilted plate 60 is placed so that the incidence surface 62 and the specimen 2 overlap each other when viewed in the direction perpendicular to the incidence surface 62 (see the arrow illustrated in FIG. 7). The tilted plate 60 can thus be placed so that the incidence surface 62 faces the surface 2a of the specimen 2. The step that places the tilted plate 60 (step S22) is performed in the same manner as the step that places the tilted plate 60 (step S12) illustrated in FIG. 2, except that the tilted plate 60 is placed so that the incidence surface 62 of the tilted plate 60 faces the specimen 2.

Note that the step that places the tilted plate 60 (step S22) may be performed before the step that positions the specimen 2 (step S20) as long as the step that places the tilted plate 60 (step S22) is performed before the step that applies the ion beam (step S23).

The ion beam is then applied to the specimen 2 (step S23).

The ion beam is generated by the ion beam generator 10, and applied to the specimen 2.

As illustrated in FIG. 8, the part of the specimen 2 that is not covered with the shield plate 30 is gradually mill by the ion beam. The ion beam that has passed by the specimen 2 is applied to the tilted plate 60 through the through-hole 22, the through-hole 42, and the through-hole 52.

The material that forms the tilted plate 60 is sputtered when the ion beam is applied to the incidence surface 62 of the tilted plate 60. In this case, most of the material that forms the tilted plate 60 that has been sputtered travels in the direction perpendicular to the incidence surface 62 (see FIG. 8). Since the tilted plate 60 is placed so that the incidence surface 62 and the specimen 2 overlap each other when viewed in the direction perpendicular to the incidence surface 62, it is possible to cause the material that forms the tilted plate 60 that has been sputtered to adhere to the surface 2a of the specimen 2.

A cross section of the specimen 2 can be prepared using the specimen preparation device 200 by performing the above steps.

The specimen preparation device 200 has the following features, for example.

The specimen preparation device 200 includes the tilted plate 60 that is placed to intersect the path of the ion beam on the downstream side of the specimen 2, and has the incidence surface 62 that is tilted relative to the direction in which the ion beam is incident. Therefore, the specimen preparation device 200 can reduce contamination of the specimen 2 in the same manner as the specimen preparation device 100.

The specimen preparation device 200 is configured so that the incidence surface 62 of the tilted plate 60 and the specimen 2 overlap each other when viewed in the direction perpendicular to the incidence surface 62 of the tilted plate 60. Therefore, the material that forms the tilted plate 60 that has been sputtered can be caused to adhere to the surface 2a of the specimen 2. The specimen preparation device 200 can thus form the desired film on the surface 2a of the specimen 2 while preparing a cross section of the specimen 2.

The incidence surface 62 of the tilted plate 60 included in the specimen preparation device 200 is formed of graphite. A carbon film can be formed on the surface 2a of the specimen 2 by sputtering graphite using the ion beam. Therefore, the specimen preparation device 200 can prepare a cross section of the specimen 2 that is observed or analyzed using an electron microscope while forming a carbon film that exhibits an antistatic effect when observing or analyzing the specimen 2 using an electron microscope or the like, for example.

3. Third Embodiment

Figure 9:
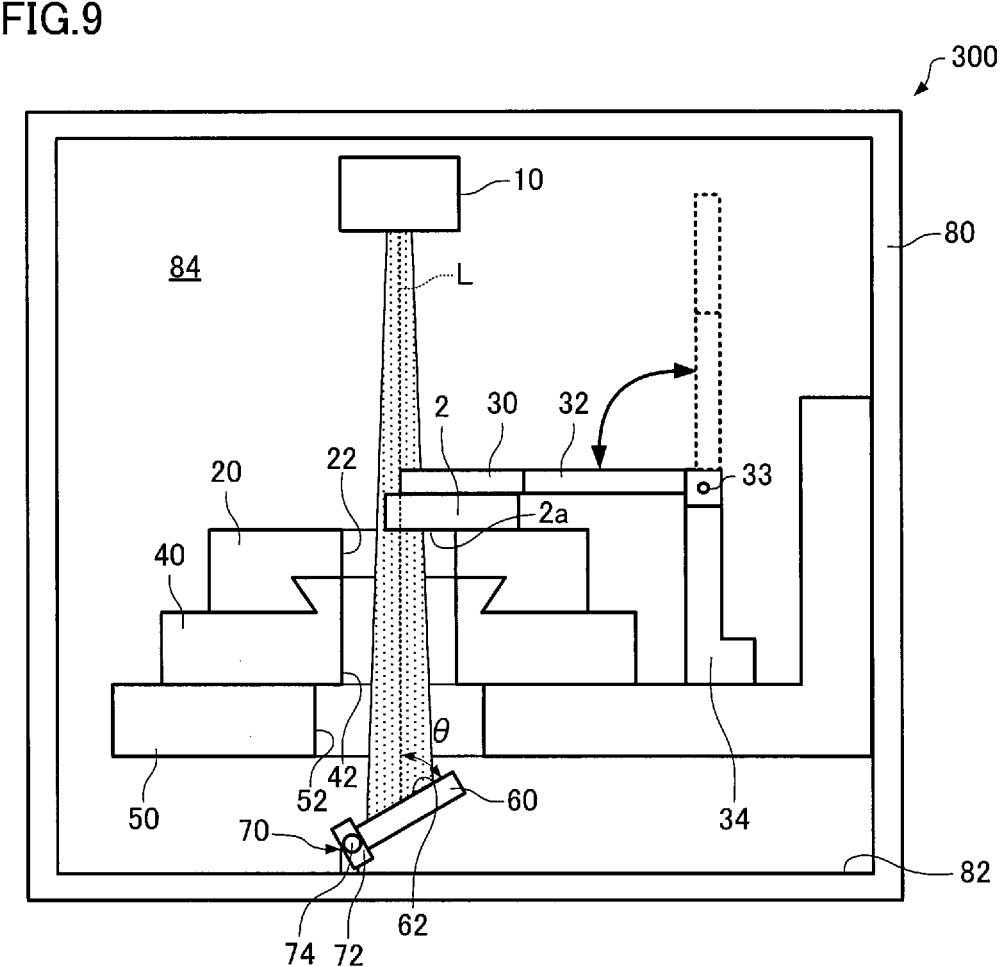
FIG. 9 schematically illustrates the configuration of a specimen preparation device according to the third embodiment.

A specimen preparation device according to a third embodiment of the invention is described below with reference to FIG. 9. FIG. 9 schematically illustrates the configuration of a specimen preparation device 300 according to the third embodiment. Note that the members of the specimen preparation device 300 according to the third embodiment that are identical in function to those of the specimen preparation device 100 according to the first embodiment are indicated by the same reference signs, and detailed description thereof is omitted.

In the specimen preparation device 300 illustrated in FIG. 9, the tilted plate support 70 supports the tilted plate 60 so that the tilt angle θ of the incidence surface 62 can be changed.

The tilted plate support 70 supports the tilted plate 60 so that the tilt angle θ of the incidence surface 62 can be changed. The tilted plate support 70 can tilt the tilted plate 60 around a shaft 74 that is provided at one end of the tilted plate 60.

A specimen preparation method that utilizes the specimen preparation device 300 is implemented in the same manner as the specimen preparation method that utilizes the specimen preparation device 100 (see FIG. 2), except that the step that places the tilted plate 60 (step S12) adjusts the tilt angle θ of the tilted plate 60 (incidence surface 62) so that the material that forms the tilted plate 60 that has been sputtered by the ion beam does not adhere to the surface 2a of the specimen 2 taking account of the shape of the specimen 2, the processing conditions, and the like, and description thereof is omitted.

The specimen preparation device 300 can achieve the same advantageous effects as those achieved by the specimen preparation device 100.

Since the specimen preparation device 300 is configured so that the tilt angle θ of the incidence surface 62 can be changed, it is possible to adjust the tilt angle θ of the incidence surface 62 so that the material that forms the tilted plate 60 that has been sputtered by the ion beam does not adhere (rarely adheres) to the surface 2a of the specimen 2 taking account of the shape of the specimen 2, the processing conditions, and the like, for example.

4. Fourth Embodiment

Figure 10:
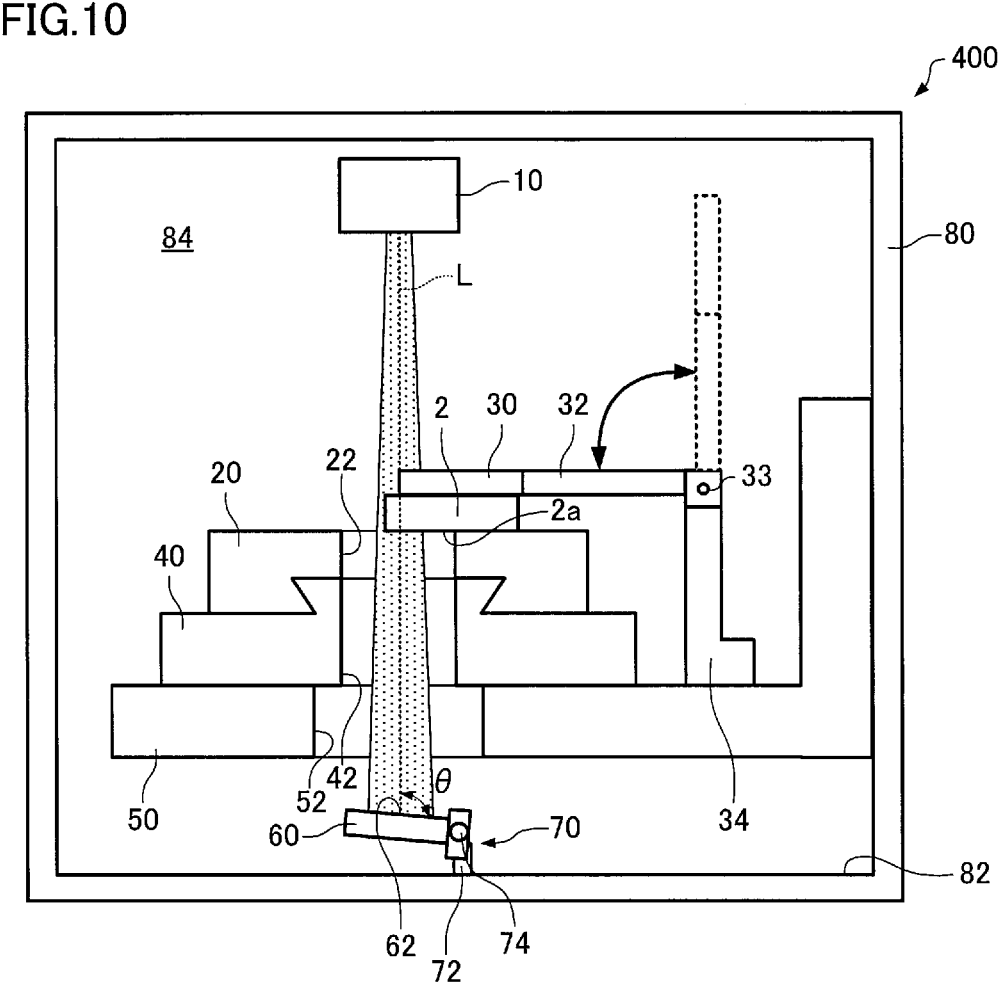
FIG. 10 schematically illustrates the configuration of a specimen preparation device according to the fourth embodiment.

A specimen preparation device according to a fourth embodiment of the invention is described below with reference to FIG. 10. FIG. 10 schematically illustrates the configuration of a specimen preparation device 400 according to the fourth embodiment. Note that the members of the specimen preparation device 400 according to the fourth embodiment that are identical in function to those of the specimen preparation device 200 according to the second embodiment are indicated by the same reference signs, and detailed description thereof is omitted.

In the specimen preparation device 400 illustrated in FIG. 10, the tilted plate support 70 supports the tilted plate 60 so that the tilt angle θ of the incidence surface 62 can be changed.

The configuration of the tilted plate support 70 is the same as the configuration of the tilted plate support 70 included in the specimen preparation device 300 according to the third embodiment, and description thereof is omitted.

A specimen preparation method that utilizes the specimen preparation device 400 is implemented in the same manner as the specimen preparation method that utilizes the specimen preparation device 200 (see FIG. 6), except that the step that places the tilted plate 60 (step S22) adjusts the tilt angle θ of the tilted plate 60 (incidence surface 62) so that the material that forms the tilted plate 60 that has been sputtered by the ion beam adheres to the surface 2a of the specimen 2 taking account of the shape of the specimen 2, the processing conditions, and the like, and description thereof is omitted.

The specimen preparation device 400 can achieve the same advantageous effects as those achieved by the specimen preparation device 200.

Since the specimen preparation device 400 is configured so that the tilt angle θ of the incidence surface 62 can be changed, it is possible to adjust the tilt angle θ of the incidence surface 62 so that the material that forms the tilted plate 60 that has been sputtered by the ion beam adheres (further adheres) to the surface 2a of the specimen 2 taking account of the shape of the specimen 2, the processing conditions, and the like, for example.

5. Fifth Embodiment

Figure 11:
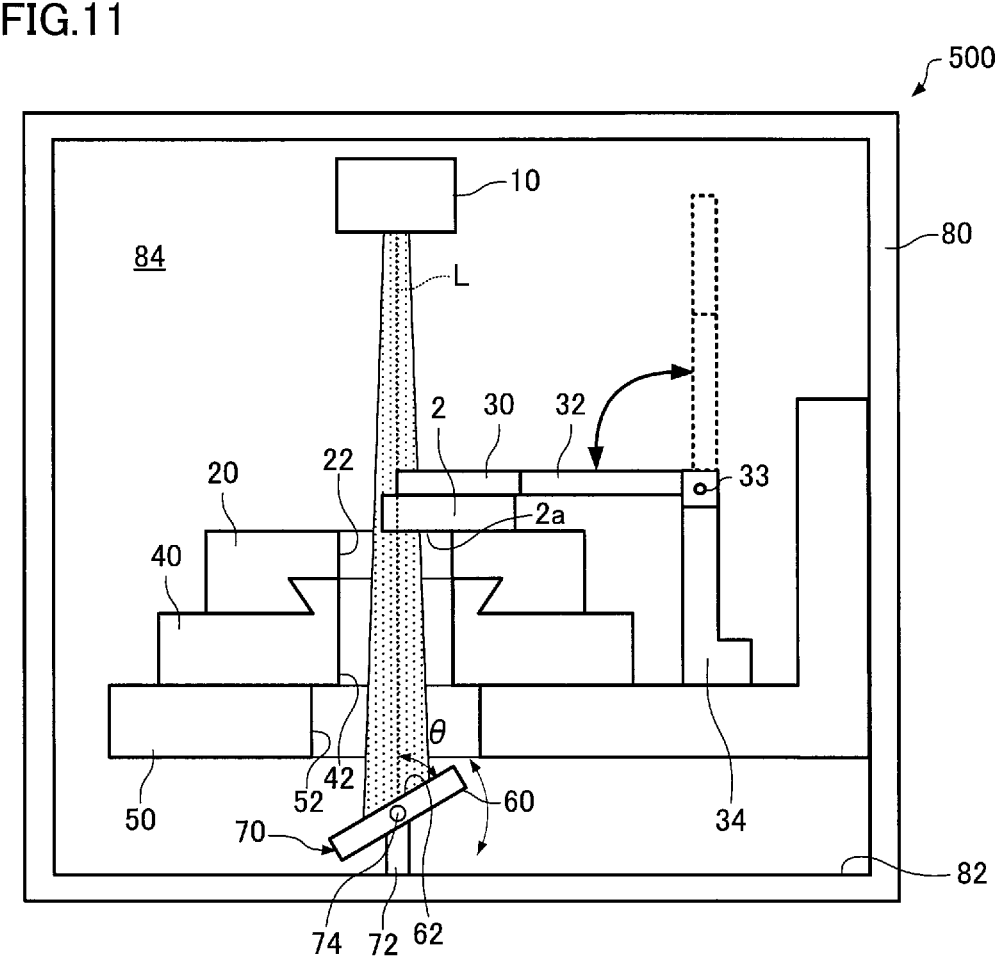
FIG. 11 schematically illustrates the configuration of a specimen preparation device the fifth embodiment.

A specimen preparation device according to a fifth embodiment of the invention is described below with reference to FIG. 11. FIG. 11 schematically illustrates the configuration of a specimen preparation device 500 according to the fifth embodiment. Note that the members of the specimen preparation device 500 according to the fifth embodiment that are identical in function to those of the specimen preparation devices 100, 200, 300, and 400 are indicated by the same reference signs, and detailed description thereof is omitted.

In the specimen preparation device 500 illustrated in FIG. 11, the tilted plate support 70 supports the tilted plate 60 so that the tilt angle θ of the incidence surface 62 can be changed. The tilted plate support 70 is provided so that the rotation shaft 74 passes through the center of the tilted plate 60. Therefore, the tilted plate support 70 can tilt the tilted plate 60 around the rotation shaft 74 in a seesaw-like manner. This makes it possible to tilt the tilted plate 60 so that the incidence surface 62 does not face the specimen 2, or tilt the tilted plate 60 so that the incidence surface 62 faces the specimen 2.

The tilted plate support 70 can also position the incidence surface 62 horizontally. Specifically, the tilt angle θ of the incidence surface 62 can be set to 90° (θ=90°). In this case, the material that forms the tilted plate 60 can be caused to adhere to the surface 2a of the specimen 2 in the same manner as in the case where the tilted plate 60 is tilted so that the incidence surface 62 faces the specimen 2.

The tilted plate support 70 includes the tilted plate holder 72, and the tilted plate 60 is attached to the tilted plate holder 72 so that the tilted plate 60 can be replaced. Therefore, the tilted plate 60 can be easily replaced. This means that the material for forming the tilted plate 60 can be easily changed. For example, a material (e.g., diamond) that is not easily affected by the ion beam may be used as the material for forming the tilted plate 60, or a material (e.g., graphite) that is caused to adhere to the surface 2a of the specimen 2 may be used as the material for forming the tilted plate 60.

For example, diamond-like carbon may be used as the material for forming the incidence surface 62. When diamond-like carbon is used as the material for forming the incidence surface 62, the incidence surface 62 is not easily sputtered by the ion beam. When diamond-like carbon is sputtered by the ion beam, a conductive film is formed on the surface 2a of the specimen 2.

The operation of the specimen preparation device 500 is described below.

When implementing a specimen preparation method that utilizes the specimen preparation device 500 in a state in which the incidence surface 62 of the tilted plate 60 does not face the specimen 2, the specimen preparation method is implemented in the same manner as the specimen preparation method that utilizes the specimen preparation device 100 and the specimen preparation method that utilizes the specimen preparation device 300 (see FIG. 2, for example).

When implementing a specimen preparation method that utilizes the specimen preparation device 500 in a state in which the incidence surface 62 of the tilted plate 60 faces the specimen 2, the specimen preparation method is implemented in the same manner as the specimen preparation method that utilizes the specimen preparation device 200 and the specimen preparation method that utilizes the specimen preparation device 400 (see FIG. 6, for example).

Since the specimen preparation device 500 is configured so that the tilted plate 60 is placed to intersect the path of the ion beam on the downstream side of the specimen 2, the specimen preparation device 500 can reduce contamination of the specimen 2 in the same manner as the specimen preparation device 100.

Since the specimen preparation device 500 is configured so that the tilted plate support 70 can support the tilted plate 60 such that the incidence surface 62 and the specimen 2 do not overlap each other when viewed in the direction perpendicular to the incidence surface 62, the specimen preparation device 500 can prevent a situation in which the material that forms the tilted plate 60 that has been sputtered by the ion beam adheres to the surface 2a of the specimen 2, or reduce the amount of the material that forms the tilted plate 60 that adheres to the surface 2a of the specimen 2 in the same manner as the specimen preparation device 100 and the specimen preparation device 300.

Since the specimen preparation device 500 is configured so that the tilted plate support 70 can support the tilted plate 60 such that the incidence surface 62 and the specimen 2 overlap each other when viewed in the direction perpendicular to the incidence surface 62, the material that forms the tilted plate 60 that has been sputtered by the ion beam applied to the incidence surface 62 can be caused to adhere to the surface 2a of the specimen 2. The specimen preparation device 500 can thus form the desired film on the surface 2a of the specimen 2 while preparing a cross section of the specimen 2.

The incidence surface 62 of the tilted plate 60 included in the specimen preparation device 500 is formed of diamond-like carbon. Therefore, the tilted plate 60 is not easily sputtered by the ion beam when the tilted plate support 70 supports the tilted plate 60 so that the incidence surface 62 and the specimen 2 do not overlap each other when viewed in the direction perpendicular to the incidence surface 62.

Since the incidence surface 62 of the tilted plate 60 included in the specimen preparation device 500 is formed of diamond-like carbon, a conductive film can be formed on the surface 2a of the specimen 2 when the tilted plate support 70 supports the tilted plate 60 so that the incidence surface 62 and the specimen 2 overlap each other when viewed in the direction perpendicular to the incidence surface 62. Therefore, the specimen preparation device 500 can prepare a cross section of the specimen 2 that is observed or analyzed using an electron microscope while forming a conductive film that exhibits an antistatic effect when observing or analyzing the specimen 2 using an electron microscope or the like, for example.

6. Modification

The invention is not limited to the above embodiments. Various modifications and variations may be made without departing from the scope of the invention.

Although the specimen preparation device 100 according to the first embodiment has been described above taking an example in which the tilted plate 60 is placed between the specimen 2 and the inner bottom surface 82 of the vacuum chamber 80 (see FIGS. 1 and 3), the tilted plate 60 need not necessarily be placed between the specimen 2 and the inner bottom surface 82 of the vacuum chamber 80.

Figure 12:
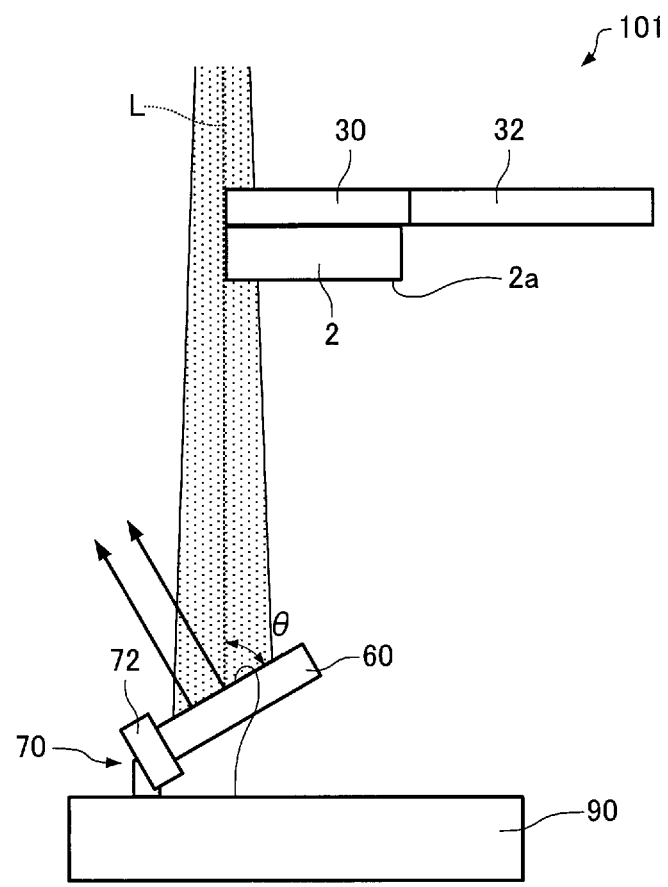
FIG. 12 schematically illustrates the configuration of a specimen preparation device according to a modification of the first embodiment.
Figure 13:
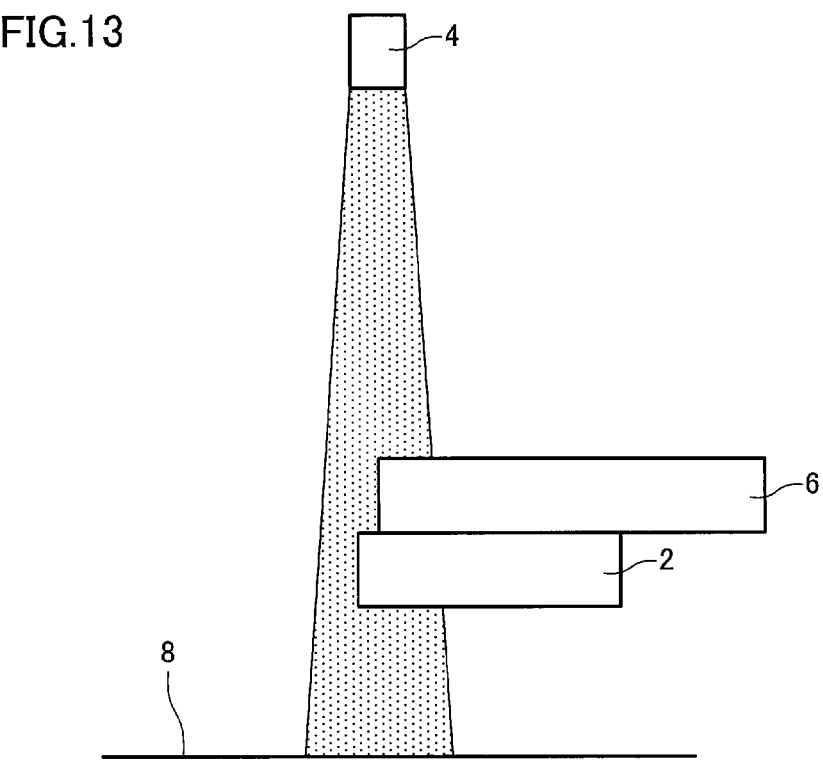
FIG. 13 schematically illustrates a state inside a vacuum chamber of a specimen preparation device.
Figure 14:
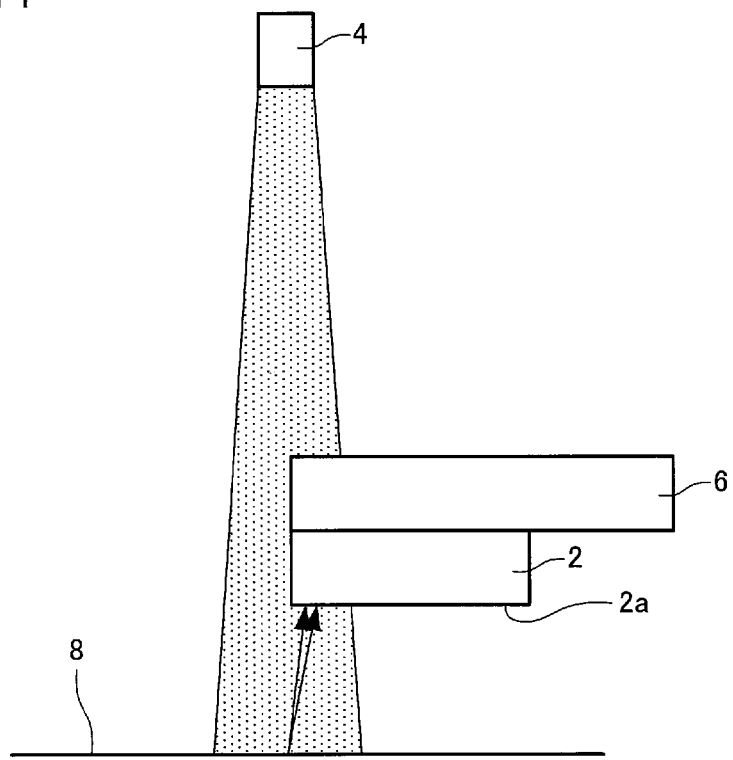
FIG. 14 schematically illustrates a state inside a vacuum chamber of a specimen preparation device.

FIG. 12 illustrates a specimen preparation device 101 according to a modification of the first embodiment. As illustrated in FIG. 12, when an additional member 90 other than the vacuum chamber is placed to intersect the path of the ion beam on the downstream side of the specimen 2 in a state in which the tilted plate 60 is not placed, the tilted plate 60 may be placed between the specimen 2 and the additional member 90. In this case, it is also possible to achieve the same advantageous effects as those achieved by the specimen preparation device 100.

The above modification may also be applied to the specimen preparation devices 200, 300, 400, and 500.

The invention includes configurations that are substantially the same (e.g., in function, method and effects, or object and effects) as the configurations described in connection with the above embodiments. The invention also includes a configuration in which an unsubstantial element described in connection with the above embodiments is replaced by another element. The invention also includes a configuration having the same effects as those of the configurations described in connection with the above embodiments, or a configuration capable of achieving the same object as those of the configurations described in connection with the above embodiments. The invention further includes a configuration obtained by adding known technology to the configurations described in connection with the above embodiments.

Although only some embodiments of the invention have been described in detail above, those skilled in the art would readily appreciate that many modifications are possible in the embodiments without materially departing from the novel teachings and advantages of the invention. Accordingly, all such modifications are intended to be included within the scope of the invention.

What is claimed is:

1. A specimen preparation device that prepares a cross section of a specimen by applying an ion beam, the specimen preparation device comprising:
   an ion beam generator that generates the ion beam;
   a specimen holder that holds the specimen;
   a shield plate positionable relative to the specimen that shields part of the specimen from the ion beam; and
   a tilted plate that is tiltable relative to the shield plate and placed to intersect a path of the ion beam not blocked by the specimen on a downstream side of the specimen, and has an incidence surface that is tilted relative to a direction in which the ion beam is incident.

2. The specimen preparation device as defined in claim 1, wherein the incidence surface and the specimen do not overlap each other when viewed in a direction perpendicular to the incidence surface.

3. The specimen preparation device as defined in claim 2, wherein the incidence surface is formed of diamond.

4. The specimen preparation device as defined in claim 1, wherein the incidence surface and the specimen overlap each other when viewed in a direction perpendicular to the incidence surface.

5. The specimen preparation device as defined in claim 4, wherein the incidence surface is formed of graphite.

6. The specimen preparation device as defined in claim 1, further comprising:
   a vacuum chamber in which the specimen is placed,
   wherein the tilted plate is placed between the specimen and an inner bottom surface of the vacuum chamber.

7. The specimen preparation device as defined in claim 1, further comprising:
   a tilted plate support that supports the tilted plate so that a tilt angle of the incidence surface relative to the ion beam can be changed.

8. A specimen preparation device that prepares a cross section of a specimen by applying an ion beam, the specimen preparation device comprising:
   an ion beam generator that generates the ion beam;
   a specimen holder that holds the specimen;
   a shield plate positionable relative to the specimen that shields part of the specimen from the ion beam;
   a tilted plate that is tiltable relative to the shield plate and placed to intersect a path of the ion beam not blocked by the specimen on a downstream side of the specimen, and has an incidence surface on which the ion beam is incident; and
   a tilted plate support that supports the tilted plate so that a tilt angle of the incidence surface relative to the ion beam can be changed.

9. The specimen preparation device as defined in claim 8, wherein the incidence surface is formed of diamond-like carbon.

* * * * *